United States Patent [19]
Ruell

[11] 4,394,773
[45] Jul. 19, 1983

[54] FINGERPRINT SENSOR

[75] Inventor: Hartwig Ruell, Mount Laurel, N.J.

[73] Assignee: Siemens Corporation, Iselin, N.J.

[21] Appl. No.: 170,606

[22] Filed: Jul. 21, 1980

[51] Int. Cl.³ .............................................. G06K 9/00
[52] U.S. Cl. ...................................... 382/4; 310/318;
310/800; 382/58
[58] Field of Search .......... 340/146.3 E, 825.3–825.34;
324/61 R, 65 R, 71 R, 71 SN, 109, 158 R;
310/311, 314, 318–319, 338, 345, 367–368, 800,
308–309; 128/734, 774; 307/400; 29/25.35;
382/4, 58

[56] References Cited

U.S. PATENT DOCUMENTS

| | | | |
|---|---|---|---|
| 3,781,855 | 12/1973 | Killen ................................. | 324/71 R |
| 3,964,014 | 6/1976 | Tehon .................................. | 310/367 |
| 3,970,862 | 7/1976 | Edelman et al. ..................... | 307/400 |
| 4,053,228 | 10/1977 | Schiller ............................... | 356/71 |
| 4,120,585 | 10/1978 | DePalma et al. .................... | 356/71 |
| 4,156,800 | 5/1979 | Sear et al. ........................... | 310/800 |
| 4,336,998 | 6/1982 | Ruell .................................... | 382/4 |
| 4,353,056 | 10/1982 | Tsikos .................................. | 382/4 |
| 4,358,677 | 11/1982 | Ruell et al. .......................... | 382/4 |

OTHER PUBLICATIONS

James, "Finger-Print Sensor", *IBM Tech. Disclosure Bulletin*, vol. 14, No. 11, Apr. 1972, p. 3361.
Mopsik et al., "Molecular Dipole Electrets", *Journal of Applied Physics*, vol. 46, No. 10, Oct. 1975, pp. 4204–4208.
Edelman, "Piezoelectric and Pyroelectric Polymer Sensors", *Proc. Conf. on Sensor Tech. for Battlefield & Physical Security Applications*, Jul. 1977, pp. 204–212.
Jet Propulsion Lab, "Transducer with a Sense of Touch", *J.P.L. Invention Report NPO–14656/30–4282*, Nov., 1979, pp. 1–7.
Staff of Reticon Corp., "Solid-State Image Sensor Array RA 100X100", Preliminary Data Sheet, 3-10-80.

*Primary Examiner*—Leo H. Boudreau
*Attorney, Agent, or Firm*—Karl F. Milde, Jr.

[57] ABSTRACT

The fingerprint sensor transforms the fingerprint information of a finger under investigation into an electric output signal. The sensor incorporates a contact device or sensor plate of a piezoelectric material. This sensor plate has a contact surface. The finger exercises a contact pressure thereon and changes thereby the distribution of electric charges on the contact surface. The new charge distribution is in accordance with the fingerprint pattern of the finger. The sensor further incorporates an electric device which provides the electric output signal in accordance with the distribution of charges.

19 Claims, 12 Drawing Figures

FINGERPRINT SENSOR

BACKGROUND OF THE INVENTION

1. Field of the Invention

This invention relates in general to a device for identifying an individual by identification of his or her fingerprint(s). This invention relates in particular to a fingerprint sensor for transforming the information contained in a person's fingerprint into an electric output signal.

2. Description of the Prior Art

Fingerprint identification systems which identify the print of a finger pressed on a contact surface are well known in the art.

U.S. Pat. No. 4,053,228, for instance, discloses a finger identification apparatus containing a transparent glass plate which serves as a contact surface or fingerprint reader. A fingerprint is formed by pressing a finger against the back surface of the glass plate and holding it in a predetermined position thereon. The fingerprint is interrogated by a light beam directed through the front surface of the glass plate. The interrogating beam is partially reflected at the back surface to provide a signal beam carrying the fingerprint information. The reflected signal beam is correlated against a hologram of the same fingerprint to provide the identification.

In U.S. Pat. No. 4,120,585, another fingerprint identification system is disclosed. This system contains a pliable optical prism as a fingerprint reader. The base of the prism is physically contacted by the finger of the person under investigation. The pliable prism deforms under the applied pressure. It partially reflects a sensing light beam to a photosensitive device which is activated. The photosensitive device, in turn, activates further optical components of the fingerprint identification system. Also in this case, a fingerprint reader is used which is examined for the ridge-valley pattern of a fingerprint of the person to be identified.

In the two U.S. Patents mentioned above, the fingerprint is formed either on a glass plate or on the base of a glass prism. The fingerprint is instantly investigated by irradiation of light. Neither mechanical nor electrical storage of the fingerprint is provided. Yet, it is advisable to read the information of the fingerprint pattern into a computer. The computer then can make an investigation with regard to specific features and with regard to the identification according to some stored information. Therefore, there is a need to store the fingerprint information of a person in a computer. That requires a fingerprint sensor for transforming the fingerprint information into an electric output signal which can be fed into a computer.

The article "Piezoelectric and Pyroelectric Polymer Sensors", Proc. Conf. on Sensor Technology for Battlefield and Physical Security Applications, Fort Belvoir, VA, July 13–15, 1977, pp. 204–212 (U.S. Army Mobility Equipment Research and Development Command, Fort Belvoir, VA, July 1977) discloses synthetic organic polymers having piezoelectric properties. Piezoelectric polymers are commercially available in thin layers. They are compliant, flexible, tough, light, and relatively cheap. They can easily be attached to a surface. Rubber cement, cyanoacrylate, epoxy, or other cements can be used. One of the commonly used piezoelectric polymers is polyvinylidene fluoride (PVDF). The piezoelectric modulus of this polymer is about six times as large as for a typical piezoelectric ceramic, such as lead zirconate titanate ceramic. A piezoelectric polymer obtains its strong piezoelectric characteristics by heating the material, applying a strong electric field, and returning to room temperature with the electric field applied. Such a process results in the alignment of a significant number of electric dipoles normal to the plane of the sheet. Any stimulus that changes the thickness of the sheet will change the surface charge density on each surface. A more detailed analysis has been published in J. Appl. Phys. 46,4204 (1975). Either the charge, a short circuit current or an open circuit voltage can be measured to determine, for instance, the pressure on a sheet of piezoelectric polymer. The flexibility, light weight, and freedom from fatigue of polymers make them suitable for measuring various physical parameters, including pressures. The thinness and flexibility of polymer gauges make them feel and act mechanically very much like skin. Therefore, polymer gauges can be applied like band-aids to monitor, for instance, heart sounds and pulse rates of patients during exercise. Arrays of gauges can be used for acoustical holography. The active portion of a gauge can be cut to any reasonable size and shape needed for the measurement.

According to the paper "Piezoelectric and Pyroelectric Polymers", supra, and to U.S. Pat. No. 3,970,862, a typical sensor for measuring temperature or pressure consists of a sandwich of two thin polymer sheets. Each sheet has evaporated metal electrodes on both faces, and the sheets are cemented together so that charges of the same polarity appear on the inner faces. The center conductor of a coaxial cable is connected to the electrodes on these inner faces, and the shield of the cable is connected to the electrodes on the outer faces. In this way, all exposed surfaces are at ground potential, and the signal inside the sensor is well shielded. Yet, sensors for measuring the distribution of pressure are not disclosed in the J. Appl. Phys. article.

In the Technical Support Package entitled "Transducer With A Sense of Touch" of JET Propulsion Laboratory, California Institute of Technology, Pasadena, California, November, 1979, is disclosed a touch or pressure sensor which determines the shape and pressure distribution of an object in contact with its surface. The sensor outputs can be displayed as an array of alphanumeric symbols on a video monitor, or they can be used to develop a pressure "map" of the surface of the object. The signals can also control mechanical or electrical equipment. The touch sensor consists of a matrix of small electrodes in a metal frame overlaid with a sheet of pressure-conductive plastic. The frame which consists of many cells is held at ground potential, and a common power source is applied to the electrodes inserted into each cell. Pressure on the plastic sheet varies the conductance of the path between an electrode and the metal frame. Thus, the current flowing through the electrode generates a voltage measure of pressure across a resistor in series with the electrode. The voltages in the matrix convey information about the shape and surface contours of the object which contacts the plastic sheet. The disclosed transducer is not a fingerprint sensor in the sense of the present invention. Fingerprints shall neither be detected nor evaluated. The object is that a Mechanical Hand will be fitted with a touch sensor on one or more fingers.

SUMMARY OF THE INVENTION

1. Objects

An object of the invention is to provide a fingerprint sensor for transforming the fingerprint information of a contacting finger into an electric output signal.

Another object of the invention is to provide a fingerprint sensor the electric output signal of which represents the information contained in a fingerprint and can be read into a computer for further processing.

Another object of the invention is to provide a fingerprint sensor which is easy to assemble, requires low cost and provides a high sensitivity, and a high reliability.

Another object of the invention is to provide a fingerprint sensor that may be assembled from components which are easily commercially available.

Another object of the invention is to provide a fingerprint sensor that converts a mechanical fingerprint information directly into an electrical information without an intermediate process being necessary, such as a conversion into an optical information, and without sophisticated technologies such as optical scanners.

Still another object of the invention is to provide a fingerprint sensor which is not subject to spurious readings, especially not dependent on the influence of temperature.

Still other objects will become apparent in the course of the following description.

2. Summary

According to this invention, a fingerprint sensor for transforming the fingerprint information of a contacting finger into an electric output signal incorporates a sensing element or a contact device which is made of a piezoelectric material. The contact device has at least two surfaces. One of these surfaces is a contact surface for exercising a contact pressure thereon by means of the contact finger under investigation. Due to the contact pressure, the density of the electric charges on the surfaces will be changed according to the fingerprint pattern of the contact finger. The fingerprint sensor further comprises an electric device for determining the distribution of charges of at least one of the mentioned surfaces. It provides the electric output signal in accordance with the distribution of the electric charges.

In this fingerprint sensor, the information of the fingerprint is directly transformed from a mechanical information (impression on the contact device) into an electric information (output signal of the electric device.)

The contact device is preferably made of a flexible piezoelectric polymer. It can also be made of a piezoelectric ceramic. If a polymer is used, preferably the well-known piezoelectric polymer polyvinylidene fluoride (PVDF) or a related material can be applied. If a ceramic is used, a lead zirconate titanate ceramic can be applied, for instance containing barium titanate or triglycine sulfate.

The piezoelectric material may be structured, that is comprise an array of a matrix of pixels, in order to avoid crosstalk between adjacent valleys of the fingerprint. The segmentation may be isotropic or not.

The electric device for determining the distribution of charges may preferably be a charge reading device which is used in a charge coupled device (CCD). For example, CCD technologies are usually applied to sense the charge distribution in CCD photodetector arrays. It should be mentioned that recently a CCD matrix with $2 \cdot 10^5$ pixels on an area of a few square centimeters has been produced. This clearly indicates that CCD technology has been developed far enough for a high resolution scanning of a spatially modulated charge distribution created by a fingerprint. Details of CCD devices are, for instance, disclosed in a data sheet entitled "Solid-State Image Sensor Array RA 100×100" by EG & G Reticon, Sunnyvale, California 94086.

In operation, the finger under investigation is pressed against the contact surface. The crests of the finger relief will exercise a certain amount of pressure on the piezoelectric substance. In the regions of the crests, local charges are built up, whereas in the regions of the valleys no charges or smaller local charges are created. This means that the geometry of the skin structure of the finger is transformed into a spatially varying charge distribution. This charge distribution is detected and measured, preferably by the mentioned charged coupled device (CCD) technologies.

The simple configuration of the new fingerprint sensor incorporates all the advantages of the piezoelectric material. In case that a piezoelectric polymer is used as the contact device or sensing element, a flexible layer or sheet can be applied. Such a layer is light, is inexpensive and disposes of a great dynamic range and an extraordinary sensitivity. Such a polymer is hardly harmed by ambient conditions like salt water, soap, common organic solvents, mechanical shocks, etc.

The electric device provides an electric output signal of the information which is contained in a fingerprint. This electric signal can be fed into a computer for further processing.

The fingerprint sensor according to the invention provides for a direct transformation of a pressure distribution into electric signals. In this transformation, no further interface technology such as an optical transducer is required. As mentioned above, CCD technology can be used so that the fingerprint sensor can be designed as a solid state transducer. Hence, the sensor can be manufactured and will have a reliability like a solid state component. The sensor elements can be very small. They are inexpensive and dependable. The do not require any maintenance.

A fingerprint sensor according to the invention is wellsuited as a plug-in module for various systems, such as a door lock, a computer terminal, etc.

The foregoing and other objects, features and advantages of the invention will be apparent from the following more particular description of the preferred embodiments of the invention, as illustrated in the accompanying drawings.

DESCRIPTION OF THE PREFERRED EMBODIMENTS

Figure 1:
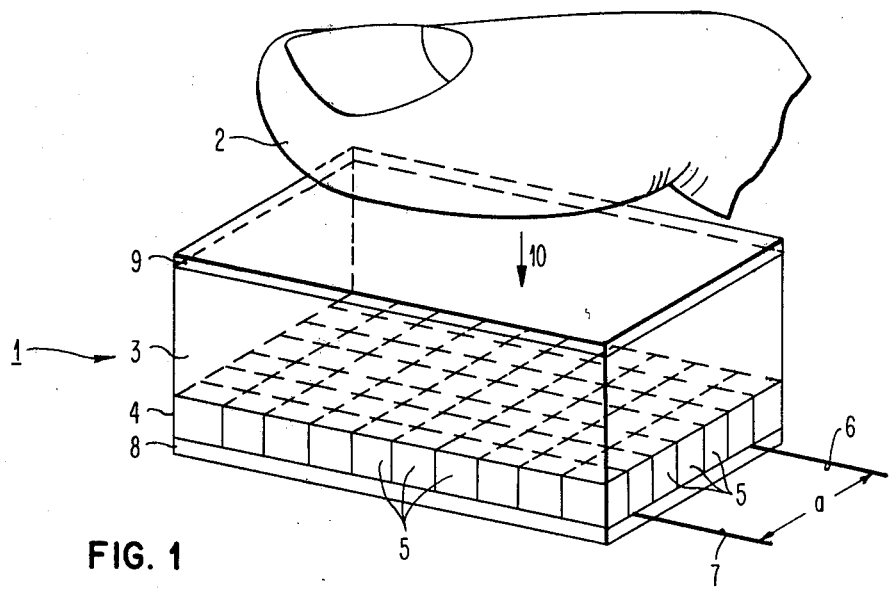
FIG. 1 is a perspective view of an embodiment of a fingerprint sensor according to the invention having a contact device containing a piezoelectric polymer or ceramic material, and a sensor matrix for determination of electric charges on the piezoelectric material.

With reference to FIG. 1, a fingerprint sensor 1 for transmitting the fingerprint information of a finger 2 into an electric output signal a is illustrated. The fingerprint sensor 1 senses the distribution of the ridges and valleys of the skin. It contains two main components: a sensing element or contact device 3 and an electrical charge measuring device 4.

The contact device 3 consists of a homogeneous piezoelectric material, for instance, a piezoelectric ceramic or, preferably, a flexible piezoelectric polymer such as polyvinylidene fluoride (PVDF). It has the shape of a rectangular sheet or layer. Attached to the lower end face of the contact device 3 is the charge determining device 4. This device 4 consists of an array of a great number of sensor elements 5. These elements 5 allow for measuring the electric charge in areas which are as small as or even smaller than the ridges and valleys of the finger 1. Therefore, there are actually used many more elements 5 than illustrated. In the embodiment of FIG. 1, the sensor elements 5 are arranged in a form of a rectangular sensor matrix. As will be explained below, also other arrangements can be chosen. The sensor matrix may be attached to the contact device by means of a cement. It may also be evaporated to the lower face end as a film, or it may have been attached in a galvanic process. Depending on the kind of device 4 which is used, also the other attachments can be applied.

As can be seen in FIG. 1, two output lines 6 and 7 are connected to the charge determining device 4 for deriving the electric output signal a which corresponds to the relief of the fingerprint.

In a specific embodiment, the lower end face of the charge determining device 4 may rest on a support sheet 8 made of an insulating material.

The upper face end of the contact device 3 may be provided with a very thin cover 9 which may be a protective coating or an electrode for determining other parameters. Such an electrode may be used, for instance, to check the temperature of the contact device 3. Such an electrode can also be used to pick up information about the heart beat of the person contacting the surface. In other words: the information can be used in an EKG for further investigation.

As soon as the finger 1 touches the upper end face of the contact device 3, and exercises some pressure thereon in the direction of the arrow 10, a inhomogenous distribution of electric dipoles is created in the contact device 3. The axes of the dipoles are arranged perpendicularly to the plane surface. The distribution of the electric charges across the surface is an exact copy of the structure of the fingerprint. That is, locations of flow density of charges correspond to valleys in the surface structure of the finger 1, whereas locations of high electron charges correspond to crests in the surface structure of the finger 1. The distribution of locations of high and low charge is sensed by the charge determining device 4. Each sensor element 5 supplies a signal corresponding to the charge of the segment of the piezoelectric material to which it is assigned. The more sensor elements 5 are present, the better and the more accurate is the information about the fingerprint. Thus, the more sensor elements are used, the higher will be the resolution.

In FIG. 1 is assumed that the charge distribution determining device 4 preferably is a charge reading device in CCD technology. Also other devices 4 can be applied, for instance a device 4 that senses the charge distribution by measuring the charges of the matrix element 5 in a scanning procedure line by line.

Figure 2:
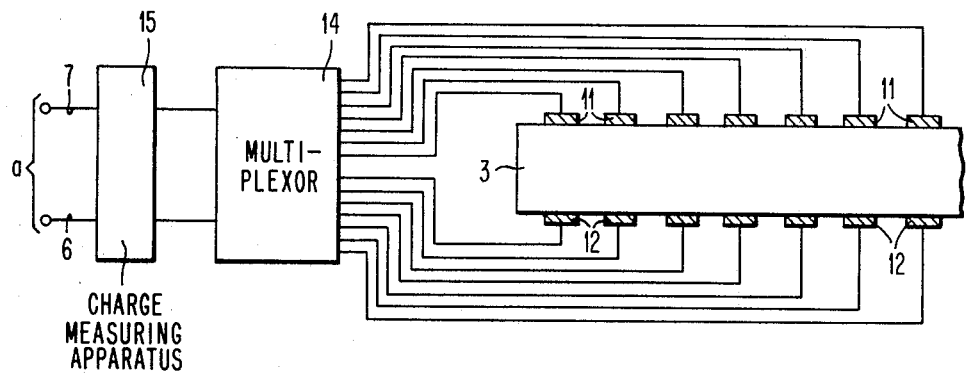
FIG. 2 is a cross-section of another embodiment of a fingerprint sensor, showing a piezoelectric contact device and a charge determining device using various electrodes.

In FIG. 2 is illustrated another embodiment of the fingerprint sensor. In this embodiment another electrical circuitry for measuring the distribution of charges on the surfaces of the contact device 3 is applied. The contact device 3, which is again made of a piezoelectric material, is provided on its upper surface with a structure or an array of small metal electrodes 11 and on its lower surface with a similar array or structure of small metal electrodes 12. Pairs of electrodes 11 and 12, respectively, are arranged oppositely to each other. The electrodes 11 and 12 are connected via connecting lines to a multiplexor 14 which in turn is connected to a charge measuring apparatus 15. The electric output signal a is supplied by the output lines 6 and 7 of the apparatus 15. In this embodiment, each sensor element 5 (as shown in FIG. 1) is made up by a specific pair of electrodes 11, 12, which is picked for measurement by the multiplexor 14, and by the charge measuring apparatus 15. Since only one charge measuring apparatus 15 is used, the electrodes 11, 12 are interrogated or scanned serially by the multiplexor 14. It is also possible to scan just a group of all electrodes 11 and 12 by one multiplexor and to scan another group by another multiplexor.

Figure 3:
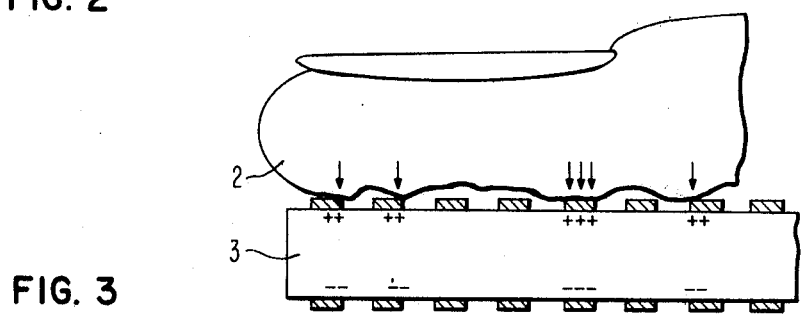
FIG. 3 is a cross-section of the contact device according to FIG. 2 under pressure of a finger.

In FIG. 3 is illustrated that the finger 1 exercises a spatially varying pressure field on the contact device 3 in accordance with the ridges and valleys of the skin surface. This pressure field will cause a locally changing charge distribution, which is illustrated in FIG. 3 by some plus and minus symbols. The charges cannot flow away, since the contact device 3 is an insulator.

Figure 4:
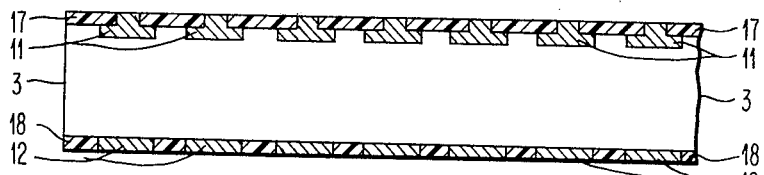
FIG. 4 is a partial cross-section of another embodiment of the contact device.

In FIG. 4 is shown another embodiment of the fingerprint sensor. As can be seen, the cross-section of the upper electrodes 11 is an inverted T, whereas the cross-section of the lower electrodes 12 is rectangular. These electrodes 12 are flat disks. As illustrated, there is provided an electrically non-conductive material 17 and 18 between adjacent electrodes 11 and 12, respectively. Insertion of the dielectric filling material 17 and 18 prevents leaking currents. In addition, the filling material 17 and 18 provides for a good mechanical strength in the electrode arrays.

Figure 5:
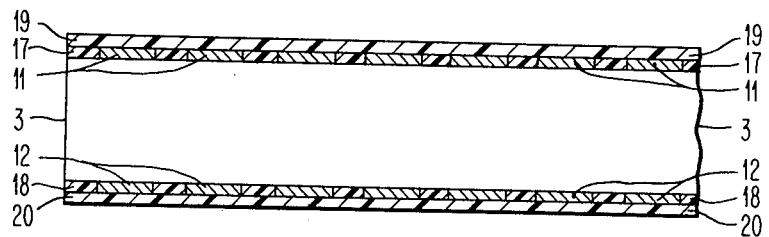
FIG. 5 is a partial cross-section of still another embodiment of the contact device.

In FIG. 5 is illustrated still another fingerprint sensor according to the invention. Also in this sensor electrodes 11 and 12 are provided on both sides of the contact device 3. The electrodes 11, 12 are all designed either as small cylindrical disks or as small rectangular pieces. Again, a dielectric filling material 17 and 18 is inserted between the electrodes 11 and 12, respectively. Thin foils 19 and 20 protect the electrodes 11 and 12, respectively, and the filling material 17 and 18, respectively, from dirt and wear and tear. The foils 19 and 20 each consist of a dielectric material. The foil 19 is preferably a pressure conductive plastic foil 19, which is able to transmit the finger pressure without any attenuation in the direction of the arrows towards the electrodes 11. The upper protection foil 19 can be made out of MYLAR. The lower foil 20 is just a protection foil made of a less expensive plastic.

Figure 6:
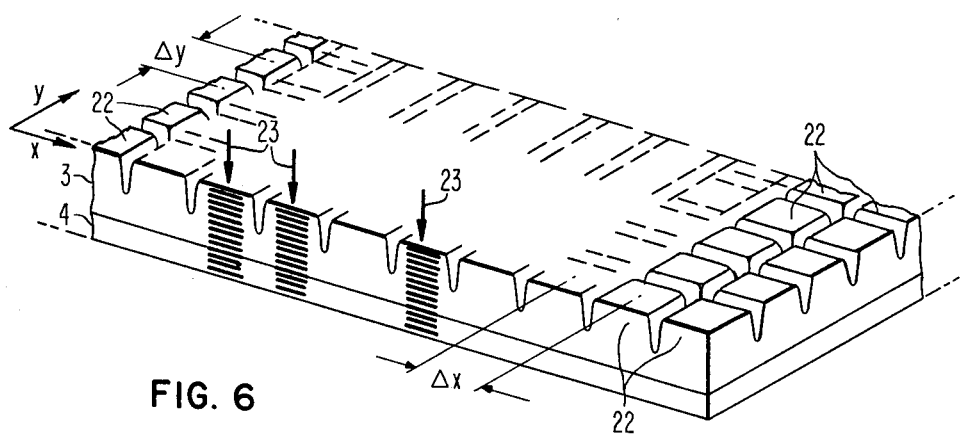
FIG. 6 is a perspective view of still another embodiment of a fingerprint sensor containing a contact device made of a piezoelectric polymer or ceramic which is structured in the form of a matrix, and a sensor matrix for determining the distribution of the charges.
Figure 7:
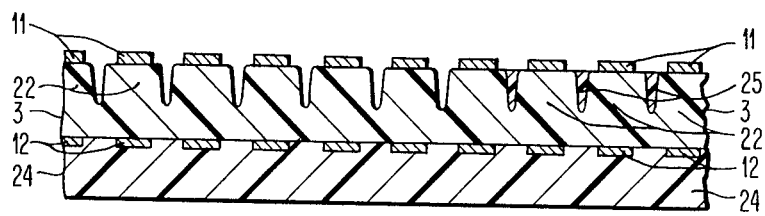
FIG. 7 is a cross-section of another embodiment of a structured contact device.

In FIGS. 6 and 7 are shown another two versions of a fingerprint sensor according to the invention. These fingerprint sensors each contain also a contact device 3 and a charge distribution measuring device 4, which is in FIG. 6 in the form of a sensor matrix. In these two versions, the upper surface of the contact device 3 contains a certain structure. The surface is structured similar to a bar of chocolate. That is, it comprises a multitude of pixels or segments 22. These segments 22 may have a rectangular or round shape. They are separated from each other by "ditches", the depth of which may equal to approximately half the thickness of the contact device 3. The pixels or segments 22 may form a rectangular matrix. The size of this matrix corresponds in FIG. 6 to the sensor matrix of the electrical charge determining device 4. The application of segments 22 will avoid crosstalk between adjacent areas, that is the "ditches" prevent to a certain degree the transportation of charges from one pixel 22 to the adjacents pixels 22.

In the cross section of FIG. 7, a charge determining device 4 having electrodes 11 and 12 is chosen. The lower electrodes 12 are embedded in an insulator support plate 24 which is attached to the contact device 3.

As indicated on the right side of FIG. 7, the "ditches" may be filled with a suitable non-conducting material 25. By using such a material 25, the insulation between adjacent pixels 22 can be improved.

In FIG. 6 is indicated that according to the valleys and crests in the finger structure, a more or less significant pressure is exercised on the segments or pixels 22. It is assumed that three side segments 22 are exposed to a significant contact pressure by some finger crests. The pressure is indicated by three arrows 23. The pressure in the direction of the arrows 23 results in an electric charge on the opposite surfaces of the three segments 22 concerned. In FIG. 6, this charge is detected by those three matrix elements of the device 4 which are assigned to the segments 22 under pressure.

As can be seen in the perspective representation of FIG. 6, the fingerprint sensor extends in two directions x and y which are perpendicular to each other. Of importance to the design of the fingerprint sensor is the proportioning of the pixels or segments 22 and their distance with respect to each other. On the one hand, the pixels 22 should have an area as large as possible to achieve a high pressure sensitivity. On the other hand, the pixels 22 should not exceed a certain magnitude, because otherwise the local resolution of the fingerprint sensor would become too poor and consequently fine structures in a fingerprint cannot be detected. Such fine structures, for instance, frequently occur in the fingerprints of oriental women.

Figure 8:
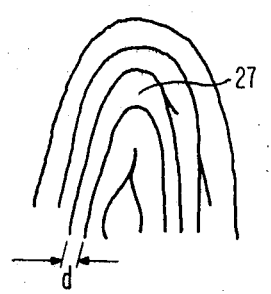
FIG. 8 is a fingerprint.

For the distance $\Delta x$, $\Delta y$ of adjacent pixels 22, the condition (1):

$$\Delta x, \Delta y \leq d \qquad (1)$$

should be observed, according to the sampling theorem. Herein, the quantity d characterizes the smallest detail that should be detected by the fingerprint sensor. According to the fingerprint in FIG. 8, the quantity d is the smallest distance between the valleys of the fingerprint.

In case of an array of equidistant pixels 22, the condition (2):

$$\Delta x = \Delta y \leq d/2 \qquad (2)$$

should be observed, according to the spatial sampling theorem.

Figure 9:
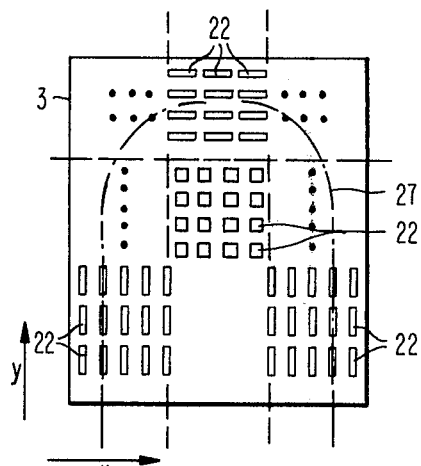
FIG. 9 is a top view of a sensor surface having pixels arranged according to the structure of a fingerprint.

In FIG. 9 is illustrated a top view of a fingerprint sensor having a multitude of pixels 22. Only few groups of all pixels 22 are represented for the sake of a clear illustration. As can be seen in FIG. 9, the pixels 22 do not necessarily have to have a square shape, and the arrangement does not necessarily have to be such that all pixels 22 have all the same distance from each other. As illustrated, the shape and the arrangement of the pixels 22 may be, at least to a certain degree and in certain groups, matched to the structure of the crests and valleys of the human fingerprint.

At the left and right side of the superimposed fingerprint 27, the valleys and crests are arranged approximately parallel to the vertical y-axis. At the upper end of the structure field of the fingerprint, the valleys and crests are arranged horizontally, that is parallel to the x-axis. The pixels 22 (along with the electrodes 11 and 12) at the left and right side and at the upper end are designed rectangularly. They follow with their longitudinal axes the structure of the crests and valleys.

In the center or core of the fingerprint 27, a high local resolution is required. In this central area, smaller pixels 22 and smaller electrodes 11 and 12 are located with a high packing density. These pixels 22 may have a square surface.

Figure 10:
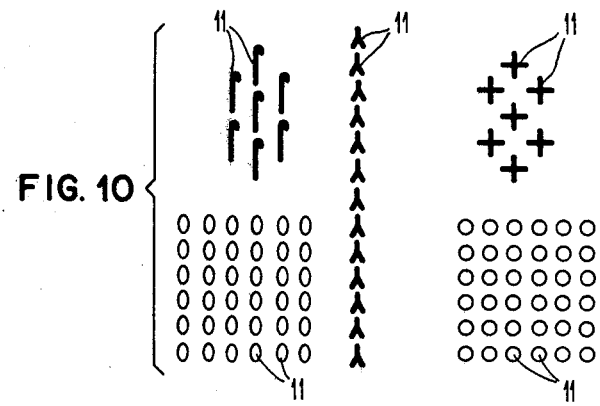
FIG. 10 is a view of various pixels or electrodes.

In FIG. 10 various designs of the electrodes 11 and/or the pixels 22 are shown. Accordingly, the electrodes 11 may be circular or elliptic discs, they may have the form of an "L", of a star, a cross, and so on.

Of importance is also that the electrodes 11 do not necessarily have to be arranged in the form of a chessboard. On the contrary, other suitable structures can be chosen, which are matched to the surface structure of the human fingerprint. Concentric rings, spirals, and other forms are applicable. The electrodes 11 may be arranged along the tangent field of a standard finger.

Figure 11:
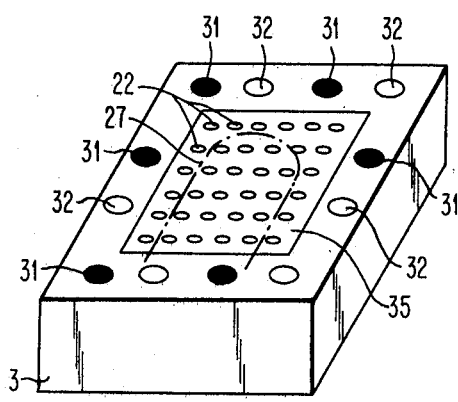
FIG. 11 is a flat fingerprint sensor having emitters and receivers distributed on its rim.

In FIG. 11 is shown a rectangular array of sensor pixels 22 which is surrounded by a rim containing various pairs of infrared (IR) emitters 31 and infrared (IR) receivers 32. The emitters 31 preferably emit radiation in the near infrared. The IR emitters 31 may be LEDs, and the IR receivers 32 may be photo diodes. Both components have only small dimensions and can easily be disposed on the rim next to the sensor surface. As soon as a finger approaches the sensor surface 35, the infrared radiation, either a pulse or a constant radiation, is emitted into the interior of the finger. The radiation remitted by the finger is received by the coordinated receiver 32 and transformed into an electrical signal such as electrical pulses.

The emitters 31 and the receivers 32 may have two functions: they may be part of a position detecting and signaling device, and simultaneously they may be part of a detector of artifacts.

The IR emitters 31 and the IR receivers 32 are connected to a first circuitry (not shown). This first circuitry allows for checking the position of the finger when it touches the sensor surface 35. Checking of the finger position should be performed before the fingerprint is investigated by means of the pressure sensitive segments 22 of the contact device 3. If the finger is not positioned correctly in the middle of the sensing surface, the first circuitry will indicate the error and activate an alarm device, for instance an optical or an acoustical device like a lamp or a loudspeaker, respectively. The alarm may cause a correction of the finger position.

A simple embodiment of the first circuitry or position indicator (not shown) would comprise a switch and an optical signal device (such as a small lamp or a LED) associated with each pair of emitters 31 and receivers 32. The optical signal device may be located on the rim close to the emitter/receiver pair 31, 32, to which it is associated. If the finger is not positioned close to a particular emitter/receiver pair 31, 32, the switch will not be actuated by the receiver 32 due to the lack of a sufficiently strong signal, and therefore the associated optical signal device will not be energized from a suitable source. A non-energized signal device will indicate that the position of the finger with respect to the particular signal device is not correct and that a correction is required. If, however, the finger is positioned correctly, the receiver 32 will obtain sufficient light to actuate the switch which in turn will cause the signal device to emit an optical signal, such as a flashing signal. This signal will indicate that the finger position is now correct.

The IR emitters 31 and the IR receivers 32 may also be connected to a second circuitry (not shown). This second circuitry is a protection circuit which allows for determining whether a vivid finger or an artifact contacts the sensor surface. From the light signal which is received by the receiver 32, the pulse frequency of the individual touching the sensor will be determined. Only in a case where the second circuitry has found out that a pulse frequency prevails and that therefore a vivid finger touches the fingerprint sensor, the fingerprint verification process proper will be started.

The second circuitry may comprise a low pass filter which blocks dc and high frequencies. As soon as the filter indicates that a low frequency contained in the frequency range of the human pulse is present, the output signal of the filter will control a gate which in turn will start the identification procedure.

Figure 12:
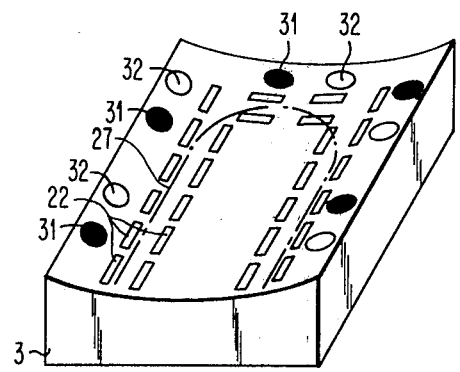
FIG. 12 is a curved fingerprint sensor.

In FIG. 12 is shown another embodiment of the fingerprint sensor. Whereas the contact surface 35 of the sensor in FIG. 11 is plane, the contact surface 35 of the sensor in FIG. 12 is now curved. The shape of the surface 35 is matched to the geometry of the finger. Again, on the rim of the sensor, there may be positioned various emitters 31 and receivers 32.

While the forms of a fingerprint sensor herein described constitute preferred embodiments of the invention, it is to be understood that the invention is not limited to these precise forms of assembly, and that a variety of changes may be made therein without departing from the scope of the invention.

What is claimed is:

1. A fingerprint sensor for transforming the fingerprint information of a finger under investigation into an electric output signal, comprising in combination:
   (a) a contact device containing a piezoelectric material, said contact device having surfaces including a contact surface for exercising a contact pressure thereon by means of said finger, thereby changing the density of electric charges on said surfaces according to the fingerprint pattern of said finger; and
   (b) electrical means for providing the electric output signal in accordance with the distribution of said charges on at least one of said surfaces.

2. The fingerprint sensor according to claim 1, wherein said contact device contains a piezoelectric polymer.

3. The fingerprint sensor according to claim 2, wherein said piezoelectric polymer is polyvinylidene fluoride.

4. The fingerprint sensor according to claim 2, wherein the contact device is a layer of a piezoelectric polymer having a first and a second surface, the first surface having said contact surface for exercising a contact pressure thereon and the second surface being scanned by said electrical means for determining the distribution of electric charges.

5. The fingerprint sensor according to claim 2, comprising,
   (a) a plate of a piezoelectric polymer having electric dipoles with their dipole axes arranged normally to the plane of said plate;
   (b) an array of electric sensor elements attached to said plate; and
   (c) means for determining the charge on said sensor elements to form said electric output signal.

6. The fingerprint sensor according to claim 5, wherein said sensor elements are arranged as a sensor matrix.

7. The fingerprint sensor according to claim 5, wherein said electric sensor elements are arranged in a structure similar to the structure of a fingerprint.

8. The fingerprint sensor according to claim 1, wherein said contact device is a plate of a piezoelectric material, said plate having a first surface for exercising said contact pressure thereon, and a second surface, whereby said first surface is structured and contains a multitude of pixels.

9. The fingerprint sensor according to claim 8, wherein said pixels are provided with small electrodes.

10. The fingerprint sensor according to claim 8, wherein an insulating material is provided between adjacent pixels.

11. The fingerprint sensor according to claim 1, further comprising a thin protective coating on said contact surface.

12. The fingerprint sensor according to claim 1, further comprising a plurality of metal electrodes on said contact surface for deriving the electric charges from said surface.

13. The fingerprint sensor according to claim 1, wherein said contact device contains a piezoelectric ceramic.

14. The fingerprint sensor according to claim 13, wherein said piezoelectric ceramic is a lead zirconate titanate ceramic.

15. The fingerprint sensor according to claim 14, wherein said ceramic contains barium titanate.

16. The fingerprint sensor according to claim 14, wherein said ceramic contains triglycine sulfate.

17. The fingerprint sensor according to claim 12, wherein said electrodes are separated from each other by an insulating material.

18. The fingerprint sensor according to claim 1, wherein said electrical means comprise a CCD scanner for determining the distribution of said charges.

19. The fingerprint sensor according to claim 1, further comprising light emitters and light receivers distributed on the rim of said contact device, said light receivers receiving light from said emitters and delivering an output signal when the finger under investigation approaches said contact surface.

* * * * *